US012778738B2

(12) United States Patent
Jeon et al.

(10) Patent No.: US 12,778,738 B2
(45) Date of Patent: Nov. 3, 2026

(54) GRAFT FOR BIOLOGICAL TUBE AND SYSTEM THEREOF

(71) Applicants: THE ASAN FOUNDATION, Seoul (KR); UNIVERSITY OF ULSAN FOUNDATION FOR INDUSTRY COOPERATION, Ulsan (KR)

(72) Inventors: Jae Yong Jeon, Seoul (KR); Hwayeong Cheon, Seoul (KR); Jung Hoon Park, Gyeonggi-do (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 757 days.

(21) Appl. No.: 18/166,764

(22) Filed: Feb. 9, 2023

(65) Prior Publication Data

US 2023/0181307 A1 Jun. 15, 2023

Related U.S. Application Data

(63) Continuation of application No. PCT/KR2021/012644, filed on Sep. 15, 2021.

(30) Foreign Application Priority Data

Sep. 16, 2020 (KR) ........................ 10-2020-0119161

(51) Int. Cl.
*A61F 2/06* (2013.01)
*A61B 5/00* (2006.01)
(Continued)

(52) U.S. Cl.
CPC .......... *A61F 2/07* (2013.01); *A61F 2002/072* (2013.01); *A61F 2210/00* (2013.01); *A61F 2220/0025* (2013.01); *A61F 2220/005* (2013.01)

(58) Field of Classification Search
None
See application file for complete search history.

(56) References Cited

U.S. PATENT DOCUMENTS 6,409,743 B1 * 6/2002 Fenton, Jr. ......... A61B 17/0487 606/232
8,366,651 B2 2/2013 Dakin et al.
(Continued)

FOREIGN PATENT DOCUMENTS

CA 2669075 A1 * 4/2008 ........... A61L 29/146
CA 2724771 A1 * 11/2009 ............. A61F 2/856
(Continued)

OTHER PUBLICATIONS

International Search Report issued Dec. 30, 2021 in PCT/KR2021/012644 filed on Sep. 15, 2021, 5 pages.

*Primary Examiner* — Ann Hu
(74) *Attorney, Agent, or Firm* — Oblon, McClelland, Maier & Neustadt, L.L.P.

(57) ABSTRACT

Disclosed is a graft for a biological tube including a graft having a hollow of a specific length, having openings at opposite ends along a lengthwise direction thereof, and being contractible, and the graft is contracted to be adhered to outer peripheral surfaces of biological tubes when heat is applied to the graft in a state, in which portions of the biological tubes are inserted into the openings of the graft.

11 Claims, 7 Drawing Sheets

(51) Int. Cl.

| | |
|---|---|
| ***A61B 17/11*** | (2006.01) |
| ***A61F 2/07*** | (2013.01) |
| ***A61N 1/05*** | (2006.01) |

(56) References Cited

U.S. PATENT DOCUMENTS

| | | | | |
|---|---|---|---|---|
| 8,690,816 | B2 | 4/2014 | Dakin et al. | |
| 8,734,503 | B2 * | 5/2014 | Orion | A61F 2/064 623/1.15 |
| 8,858,577 | B2 * | 10/2014 | Kubiak | A61F 2/08 606/151 |
| 8,945,156 | B2 * | 2/2015 | Kubiak | A61F 2/08 606/151 |
| 8,961,446 | B2 | 2/2015 | Dakin et al. | |
| 9,265,632 | B2 | 2/2016 | Orion et al. | |
| 9,282,967 | B2 | 3/2016 | Paris et al. | |
| 9,345,485 | B2 | 5/2016 | Dakin et al. | |
| 9,949,852 | B2 | 4/2018 | Orion et al. | |
| 9,993,251 | B2 | 6/2018 | Todd et al. | |
| 10,004,509 | B2 | 6/2018 | Todd | |
| 10,064,625 | B2 * | 9/2018 | Kahana | A61B 17/11 |
| 10,363,040 | B2 | 7/2019 | Sambandam | |
| 10,434,293 | B2 | 10/2019 | Park et al. | |
| 10,806,458 | B2 | 10/2020 | Todd | |
| 10,987,106 | B2 | 4/2021 | Paris et al. | |
| 2005/0273121 | A1 | 12/2005 | Sato et al. | |
| 2006/0212113 | A1 * | 9/2006 | Shaolian | A61F 2/07 623/1.35 |
| 2007/0142907 | A1 * | 6/2007 | Moaddeb | A61F 2/2469 623/2.37 |
| 2007/0207186 | A1 * | 9/2007 | Scanlon | A61F 2/91 623/1.42 |
| 2008/0058579 | A1 * | 3/2008 | Hunter | A61K 49/222 600/8 |
| 2008/0221665 | A1 * | 9/2008 | Peckham | A61F 2/88 623/1.42 |
| 2009/0036817 | A1 | 2/2009 | Dakin et al. | |
| 2009/0036820 | A1 | 2/2009 | Dakin et al. | |
| 2010/0030256 | A1 * | 2/2010 | Dubrul | A61B 10/0266 606/200 |
| 2010/0166820 | A1 * | 7/2010 | Boden | C08G 63/00 528/370 |
| 2011/0230955 | A1 | 9/2011 | Orion et al. | |
| 2011/0251667 | A1 * | 10/2011 | Argentine | A61F 2/07 623/1.13 |
| 2013/0110029 | A1 | 5/2013 | Dakin et al. | |
| 2013/0190787 | A1 | 7/2013 | Paris et al. | |
| 2013/0197546 | A1 | 8/2013 | Paris et al. | |
| 2014/0067038 | A1 * | 3/2014 | Daugherty | A61F 2/07 623/1.14 |
| 2014/0180191 | A1 | 6/2014 | Dakin et al. | |
| 2014/0257462 | A1 | 9/2014 | Orion et al. | |
| 2015/0148826 | A1 | 5/2015 | Dakin et al. | |
| 2015/0223817 | A1 | 8/2015 | Paris et al. | |
| 2015/0313595 | A1 | 11/2015 | Houghton et al. | |
| 2015/0313596 | A1 | 11/2015 | Todd | |
| 2015/0313597 | A1 | 11/2015 | Sambandam | |
| 2015/0313598 | A1 | 11/2015 | Todd et al. | |
| 2015/0351768 | A1 | 12/2015 | Kahana et al. | |
| 2016/0096008 | A1 | 4/2016 | Park et al. | |
| 2016/0143754 | A1 | 5/2016 | Orion et al. | |
| 2016/0151066 | A1 | 6/2016 | Paris et al. | |
| 2016/0157989 | A1 * | 6/2016 | Wagner | A61F 2/064 623/1.38 |
| 2017/0105724 | A1 * | 4/2017 | Limem | A61B 17/064 |
| 2018/0028431 | A1 * | 2/2018 | Chiattello | C09D 5/14 |
| 2018/0064931 | A1 * | 3/2018 | Clements | A61B 5/388 |
| 2018/0242972 | A1 | 8/2018 | Todd | |
| 2018/0250009 | A1 | 9/2018 | Todd et al. | |
| 2019/0366062 | A1 | 12/2019 | Park et al. | |
| 2020/0015823 | A1 | 1/2020 | Sambandam | |
| 2020/0146680 | A1 | 5/2020 | Houghton et al. | |
| 2021/0085328 | A1 | 3/2021 | Todd | |
| 2021/0177420 | A1 | 6/2021 | Paris et al. | |

FOREIGN PATENT DOCUMENTS

| | | | | |
|---|---|---|---|---|
| EP | 1 055 401 | A1 | 11/2000 | |
| JP | 2011-528275 | A | 11/2011 | |
| JP | 2015-515329 | A | 5/2015 | |
| JP | 5855460 | B2 | 2/2016 | |
| KR | 10-2015-0104168 | A | 9/2015 | |
| WO | WO-0035352 | A1 * | 6/2000 | A61F 2/01 |
| WO | WO-0141654 | A2 * | 6/2001 | A61F 2/064 |
| WO | WO 2015/168508 | A2 | 11/2015 | |

* cited by examiner

GRAFT FOR BIOLOGICAL TUBE AND SYSTEM THEREOF

CROSS-REFERENCE TO RELATED APPLICATIONS

The present application is a continuation of International Patent Application No. PCT/KR2021/012644, filed on Sep. 15, 2021, which is based upon and claims the benefit of priority to Korean Patent Application No. 10-2020-0119161 filed on Sep. 16, 2020. The disclosures of the above-listed applications are hereby incorporated by reference herein in their entirety.

BACKGROUND

Embodiments of the inventive concept described herein relate to a graft for a biological tube and a system thereof, and more particularly, to a graft for a biological tube and a system thereof, by which opposite cut ends of a biological tissue may be fixed such that a communication state thereof is maintained while they are not wound by a restoring force even after the biological tissue is cut.

In general, a surgical blood vessel reconstructive operation is performed for exchange of blood vessels that are damaged or destroyed due to injuries or blood vessel diseases. Most of moisture of our bodies is present in cells or in blood vessels, but another portion thereof is present as a tissue liquid that gathers between the cells, is converted to lymph (liquid) that circulates to a lymphatic system, and consequently enters veins and is mixed with blood.

The lymphatic system includes all off lymphatic vessels that start from a distal portion of the body and connected to a center thereof, a lymphatic gland, in which the lymphatic vessels are concentrated, marrows and thymuses that make and adjust immunocytes, and spleen that are final terminal stations, in which immunocytes are destructed.

In particular, the lymphatic gland is a small and bean-shaped organ that filters the lymphatic liquid. The lymphatic glands are located in the whole body, but in particular, are intensively present immediately under skin in the neck, below the arms, and in the groin, and are portions of the lymphatic system that is one of a body defense mechanism that prevents infections and spreading of a cancer.

The lymph is a transparent liquid consisting of water, white blood cells, proteins, and fats, which is filtered from blood vessels to spaces between cells. A portion of the body liquid is reabsorbed by the blood vessels, but the remaining portion thereof enters the lymphatic vessels. Then, the lymph passes the lymphatic glands that are specific set point, at which damaged cells, infective microorganisms, cancer cells are filtered from the body liquid and are destructed, and the lymphatic glands are swollen when a larger number of infective microorganisms or cancer cells are present, and occasionally the microorganisms cause infection in the lymphatic gland That is, due to the malignant tumors, the lymphatic vessels or the lymphatic glands may be blocked and may be generated due to a surgery of removing the lymphatic glands together.

The lymphatic vessels that are broken during an excision of the lymphatic gland has a small diameter unlike the blood vessels having large diameters and are wound due to an elastic restoring force whereby distances between the cut portions become larger and lymphedemas are caused.

SUMMARY

An aspect of the inventive concept provides a graft for a biological tube and a system thereof, by which cut opposite ends of a biological tissue are prevented from being shrunk by an elastic restoring force and are fixed to maintain a communication state even after the biological tissue is cut.

The technical objects of the inventive concept are not limited to the above-mentioned ones, and the other unmentioned technical objects will become apparent to those skilled in the art from the following description.

According to an embodiment of the inventive concept, a graft for a biological tube includes a graft having a hollow of a specific length, having openings at opposite ends along a lengthwise direction thereof, and being contractible, and the graft is contracted to be adhered to outer peripheral surfaces of biological tubes when heat is applied to the graft in a state, in which portions of the biological tubes are inserted into the openings of the graft.

The graft may include a protrusion formed on an inner peripheral surface of the graft and protruding to a radially inner side.

The protrusion may be curved toward a center of the graft at a specific curvature.

The protrusion may include a sharp portion, a width of which becomes gradually smaller as it goes farther away from the graft.

A diameter of the graft may be larger than a diameter of the biological tube such that the biological tubes are inserted into the openings at a room temperature.

The graft may include a film layer formed on an inner peripheral surface of the graft and being broken when heat is applied thereto.

Tissue fibrosis may be restrained in a space between the film layer and an outer peripheral surface of the graft.

According to an embodiment of the inventive concept, a graft system for a biological tube includes the graft claimed in any one of claims 1 to 7, and a laser light emitting part that irradiates light to the graft, and the graft may be contracted when the light is applied thereto.

A photo-reactive material may be applied to the graft, and the graft may be contracted when the light irradiated from the laser light emitting part is applied to the photo-reactive material.

The photo-reactive material may be photo-reactive metallic nano particles.

The photo-reactive material may be formed in partial areas adhered to the biological tubes.

The photo-reactive material may be formed in an entire area of the graft.

The graft system may include grippers that grip opposite end of the biological tubes along a lengthwise direction thereof The light irradiated from the laser light emitting part may be 650 nm to 900 nm.

Detailed items of the other embodiments are included in the detailed description and the accompanying drawings.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
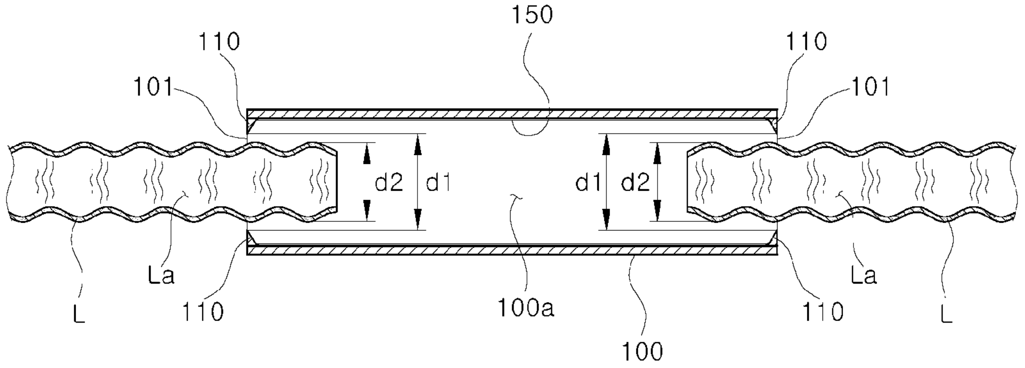
FIG. 1 is a cross-sectional view of a graft for a biological tube according to an embodiment of the inventive concept.

The above and other aspects, features, and advantages of the inventive concept will become apparent from the following description of the following embodiments given in conjunction with the accompanying drawings. However, the inventive concept is not limited by the embodiments disclosed herein but will be realized in various different forms, and the embodiments are provided only to make the disclosure of the inventive concept complete and fully inform the scope of the inventive concept to an ordinary person in the art, to which the inventive concept pertains, and the inventive concept will be defined by the scope of the claims.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other components, in addition to the aforementioned components. Throughout the specification, the same reference numerals denote the same components, and "and/or" includes the respective components and all combinations of the components. Although "first", "second" and the like are used to describe various components, the components are not limited by the terms. The terms are used simply to distinguish one component from other components. Accordingly, it is apparent that a first component mentioned in the following may be a second component without departing from the spirit of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The terms, such as "below", "beneath", "lower", "above", and "upper", which are spatially relative may be used to easily describe a correlation between one component and other components as illustrated in the drawings. The spatially relative terms have to be understood as terms including different directions of the components during use or an operation, in addition to the direction illustrated in the drawings. For example, when the components illustrated in the drawings are overturned, the components "below" or "beneath" another component may be positioned "above" the other components. Accordingly, the term "below" or "beneath" may include "below" or "beneath" and "above". The component may be oriented in different directions, and accordingly, the spatially relative terms may be construed according to the orientation.

Hereinafter, exemplary embodiments of the inventive concept will be described in detail with reference to the accompanying drawings.

Figure 2:
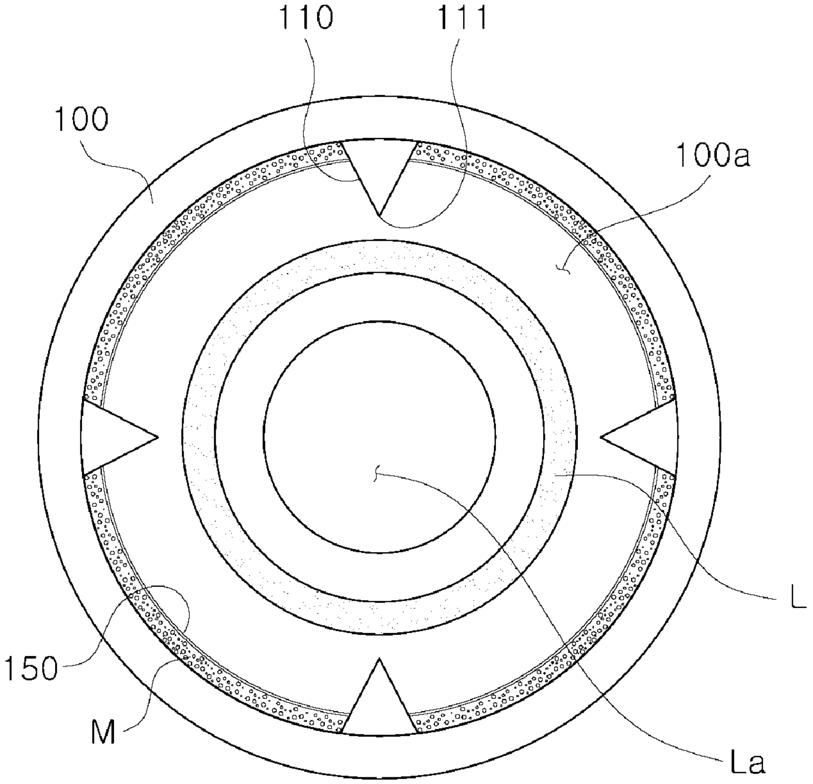
FIG. 2 is a side view of one opening of the graft of FIG. 1.
Figure 3:
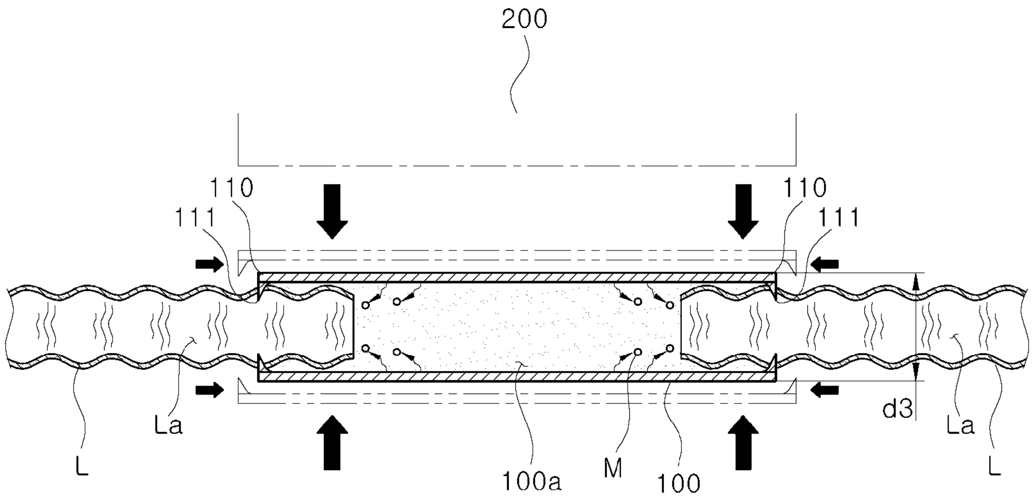
FIG. 3 illustrates a thermal contraction state of the graft of FIG. 1.

FIG. 1 is a cross-sectional view of a graft for a biological tube according to an embodiment of the inventive concept. FIG. 2 is a side view of one opening of the graft of FIG. 1. FIG. 3 illustrates a thermal contraction state of the graft of FIG. 1.

Referring to FIGS. 1 to 3, a graft for a biological tube according to an embodiment of the inventive concept may include a graft 100 that has a hollow of a specific length and has openings 101 at opposite ends along a lengthwise direction, thereof A material of the graft 100, for example, may be a tube of MIcroFit that is a registered trademark, and this may be any one of three materials of RW-175, MT1000, and MT2000 that agree with requirements of U.S. Pharmacopeia (USP) Class VII or a combination thereof.

In the case of RW-175 and MT1000, a semirigid fluoropolymer of a high-ductile property may be used. In this case, it may be suitable for an apparatus that may endure a high-temperature environment well, and has an excellent resistant force against wearing and cutting and has an excellent resistant force to various liquid-state material as well.

The RW-175 is a material that agrees with requirements of a low gas exhaustion material of NASA.

The MT1000 tube may be disinfected by radioactive rays, an ethylene oxide, vapor, and drying heat with no big change in physical characteristics.

The MT2000 tube may be formed of high-ductile modified polyolefin having flexibility, smoothness, and an excellent electrical insulation property. A low-contraction temperature of MT2000 may allow the tube to be contracted promptly as compared with another material having similar characteristics. Accordingly, a damage that may influence a base that is sensitive to temperature may be reduced.

The MT2000 tube may be disinfected by gamma radioactive rays or an ethylene oxide with no big change in physical characteristics.

The graft 100 may include the openings 101 that are formed at opposite ends along a lengthwise direction thereof Hereinafter, a case, in which the biological tubes and the biological tissues, which will be described below, are lymphatic vessels "L" and a lymphatic gland "N", will be described as an example. The openings 101 formed at the opposite ends of the graft 100 may be formed to have an inner diameter that is larger than a maximum outer diameter d2 of the lymphatic vessels "L" such that cut portions of the lymphatic vessels "L" may be inserted thereinto.

A protrusion 110 that protrudes to a radially inner side may be provided on an inner peripheral surface of the graft 100. As will be described later, when a diameter of the graft 100 is made smaller by a separate heat source, a protruding end of the protrusion 110 is pressed or stopped and fixed by an outer surface of the lymphatic vessel "L" whereby coupling of the lymphatic vessel "L" and the graft 100 is maintained.

In particular, the protrusion 110 is formed to be curved toward a hollow 100*a* of the graft 100 at a specific curvature, and in addition, when a sharp portion 111, a width of which becomes gradually smaller as the protrusion 110 becomes farther away from the graft 100, is formed, the sharp portion 111 is stopped and fixed by a portion of the outer surface of the lymphatic vessel "L" whereby a coupling force between the graft 100 and the lymphatic vessel "L" is secured.

Meanwhile, a laser light emitting part 200 (see FIG. 3) for contracting the graft 100 by applying heat may be further included. The light irradiated from the laser light emitting part 200 may be infrared ray light of 650 nm to 900 nm, which has a thermal effect, and preferably, may be light of 800 nm. In particular, the light may be light of a short wavelength, which is not harmful to human bodies and by which heat may be transferred down to a biological tissue of 1 mm or less under skin while minimizing damage to a surface of the skin or peripheral tissues because a wavelength thereof is larger than that of visual ray or infrared ray and thus it may penetrate into the human body relatively deep. Here, because the wavelength of the used light may be various wavelengths such that the light may be applied to various target points or depths from a depth of 1 mm to 3.4 mm according to an implementation environment or a target biological body, the inventive concept is not limited thereto.

Furthermore, the graft 100 may include a photo-reactive material that reacts with the light irradiated from the laser light emitting part 200 and emits heat. The photo-reactive material may be metal nano particles, and it is apparent that it may be coated on an outer surface or inner surface of the graft 100 or may be formed to be included in the material of the graft 100.

Because a sensitivity, by which the graft 100 reacts the light irradiated from the laser light emitting part 200 is variable according to an installation depth of the graft 100, heat may be generated more effectively through the photo-reactive material included in the graft 100. Then, the photo-reactive material is formed in an area of the graft 100, which is adhered to the lymphatic vessel "L" whereby heat is intensively applied to a portion of the graft 100, which is adhered to the lymphatic vessel "L" for firm coupling. This means that the protrusion 110 may be firmly connected to the lymphatic vessel "L" because the photo-reactive material is additionally included at a periphery of the opening 101 of the graft 100. Here, it is apparent that the photo-reactive material may be included in an entire area of the graft 100 when it is necessary to uniformly contract the graft 100 as a whole.

It is preferable that a minimum inner diameter d1 of the protrusion 110 of the graft 100 is larger than an inner diameter d2 of the lymphatic vessel "L" such that no interference occurs when the lymphatic vessels "L" are inserted through the openings 101 of the lymphatic vessels "L" at a room temperature.

A film layer 150 that is broken when heat is applied may be further included at an inner peripheral surface of the graft 100.

The film layer 150 may define a space with an outer peripheral surface of the graft 100, and a separate chemical "M" may be interposed in the space. The chemical "M" is a chemical that prevents tissue fibrosis at a cut portion or a peripheral portion of the lymphatic vessel "L", and when the graft 100 is contracted, the chemical "M" is discharged from the film layer 150, is discharged through the hollow **100*a* of the graft 100, and is applied to the cut portion or the peripheral portion of the lymphatic vessel "L" due to breaking of the film layer 150**.

Hereinafter, operations of the graft for a biological tube and a system thereof according to an embodiment of the inventive concept will be described sequentially.

FIGS. 4 to 7 illustrate a process of operating the graft system for a biological tube according to an embodiment of the inventive concept.

Figure 4:
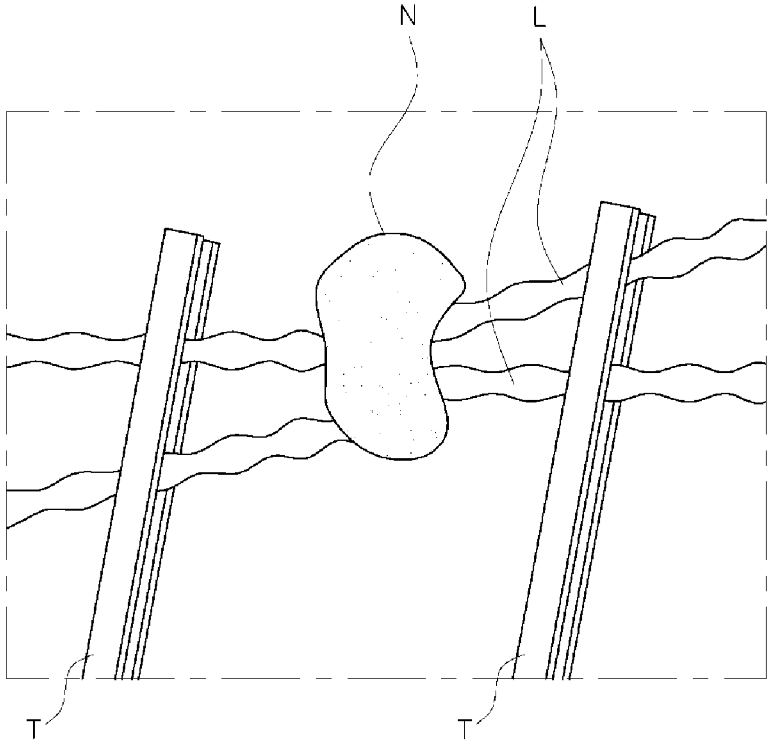
FIGS. 4 to 7 illustrate an operation process of a graft system for a biological tube according to an embodiment of the inventive concept.

First, referring to FIG. 4, the lymphatic vessel "L" and the lymphatic gland "N" that is located to be communicated with the lymphatic vessel "L" is exemplarily illustrated as an example of the above-described biological tube, but various biological tubes and excisions of biological tissues in addition to the lymphatic vessel "L" and the lymphatic gland "N" may be applied.

For an excision of the lymphatic gland "N" disposed to be communicated with the lymphatic vessel "L", opposite sides of the lymphatic vessel "L" with respect to the lymphatic gland "N" along a lengthwise direction are gripped and supported by using the grippers "T". Then, the grippers "T" may mean forceps as an example, and the grippers "T" fix the lymphatic vessels "L" located at opposite ends of the lymphatic gland "N" along a lengthwise direction, which is targeted to be excised.

Figure 5:
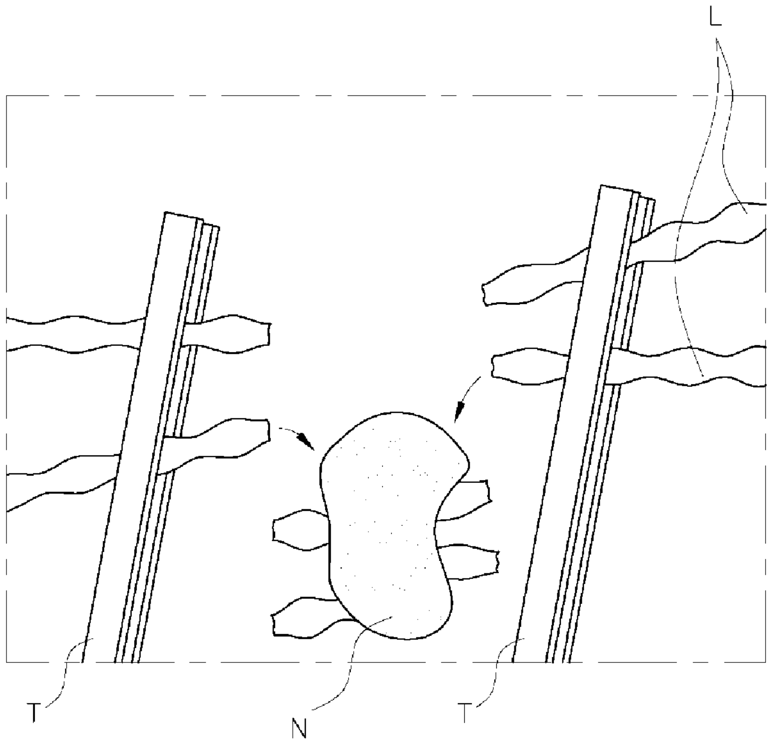

Referring to FIG. 5, the lymphatic gland "N" is removed by excising the lymphatic vessel "L" that is communicated with the lymphatic gland "N". Then, a specific restoring force acts on the lymphatic vessel "L" in a direction that becomes farther from a cut portion of the lymphatic gland "N", but the lymphatic vessel "L" is maintained in a state, in which it is fixed by the grippers "T".

Figure 6:
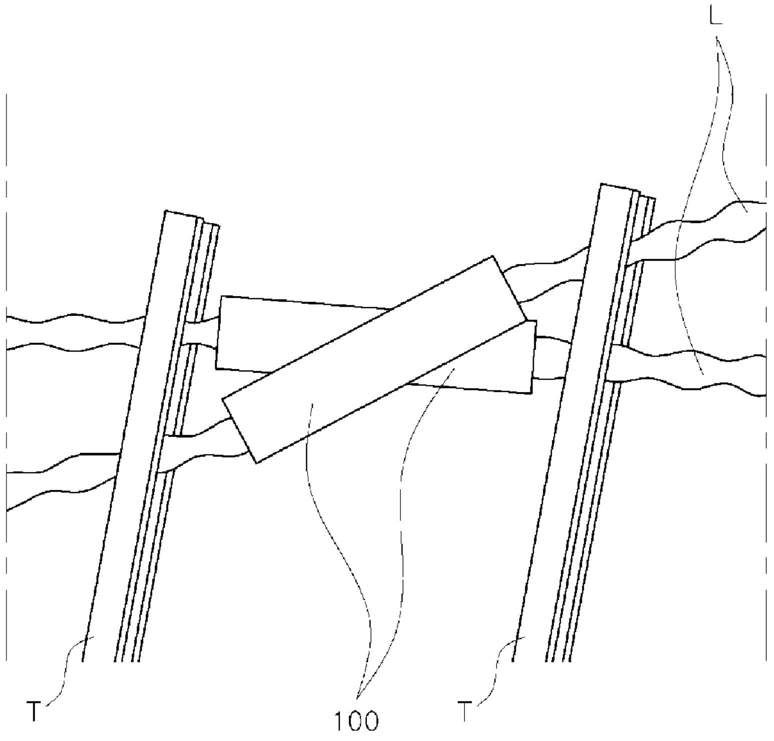

Referring to FIG. 6, the cut portions of the lymphatic vessel "L" are located to be inserted into the openings 101 of the graft 100. FIG. 6 illustrates a state, in which two grafts 100 are disposed to overlap and cross each other, as an example, but because one graft 100 may be provided if necessary but various numbers of grafts 100, such as two or more grafts 100, may be provided according to cut portions of the lymphatic gland "N", the number of the grafts 100 is not limited to a specific number.

Figure 7:
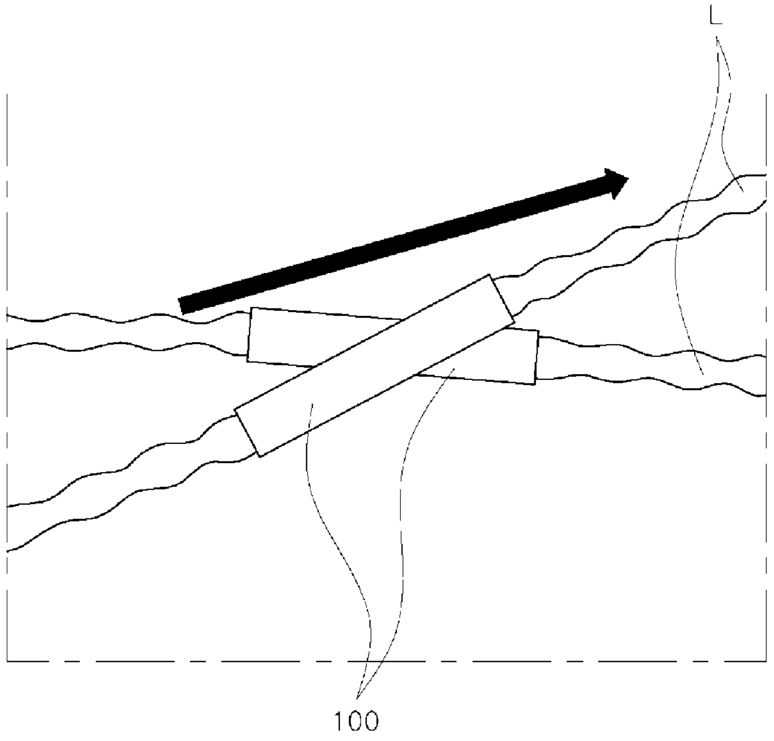

Referring to FIG. 7 together with FIG. 3, the graft 100 exhibits characteristics of being contracted when heat is applied as described above, and to achieve this, the light is irradiated by using the laser light emitting part 200 that is provided separately to induce thermal contraction of the graft 100. Then, the graft 100 may have characteristics of being contracted to two thirds of the diameter of the graft 100 when heat is applied from the outside.

Furthermore, the graft 100 is contracted in a radially inner direction and the sharp portion 111 of the protrusion 110 is adhered to or stopped by and fixed to the outer surface of the lymphatic vessel "L". Accordingly, even when the grippers "T" are removed, the lymphatic vessel "L" is maintained in a state, in which it is communicated through the graft 100. That is, because any one cut side of the lymphatic vessel "L" is communicated with the hollow **100*a* of the graft 100** and, through this, an opposite cut side of the lymphatic vessel "L" is maintained in a communication state, the flows of the lymphatic liquid may be maintained consistently.

Meanwhile, a precise control may be made such that a specific portion of the graft 100 is contracted when the graft 100 is contracted by the light provided from the laser light emitting part 200 due to the nano particles included in the graft 100, and damage to the peripheral tissues due to heat may be minimized.

Meanwhile, the chemical "M" accommodated by the film layer 150 may prevent generation of lymphedemas more effectively as the chemical that prevents fibrosis in tissues of a peripheral portion thereof with heat generated when the graft 100 is contracted when the film layer 150 is broken by the heat generated by the laser light emitting part 200 and the chemical particles are discharged from the film layer 150 at the same time. The graft 100 may be utilized as a lymphatic graft that may include flows of the lymphatic liquid even after a surgery.

Accordingly, the graft for a biological tube and the system thereof according to an embodiment of the inventive concept may prevent the biological tissues located in the middle of the biological tube from being shrunk due to an elastic restoring force after the biological tissues are cut and maintain the communication state of the lymphatic liquid.

Furthermore, a more precise contraction may be made because the graft for connecting the cut opposite ends of the biological tube has thermal contraction characteristics and irradiation of the laser is used for generation of the heat of the graft.

The effects of the inventive concept are not limited thereto, and other unmentioned effects of the inventive concept may be clearly appreciated by those skilled in the art from the following descriptions.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. A graft for a biological tube, comprising:

a graft having a hollow of a specific length, having openings at opposite ends along a lengthwise direction thereof, and being contractible, wherein the graft is configured to be contracted to be adhered to outer peripheral surfaces of biological tubes when heat is applied to the graft in a state, in which portions of the biological tubes are inserted into the openings of the graft, and wherein the graft comprises photo-reactive metallic nano particles, and the graft is configured to be contracted when a laser light is applied to the photo-reactive metallic nano particles.

2. The graft of claim 1, comprising:

a protrusion formed on an inner peripheral surface of the graft and protruding to a radially inner side.

3. The graft of claim 2, wherein the protrusion is curved toward a center of the graft at a specific curvature.

4. The graft of claim 3, wherein the protrusion includes a sharp portion, a width of which becomes gradually smaller as it goes farther away from the graft.

5. The graft of claim 1, wherein a diameter of the graft is larger than a diameter of the biological tube such that the biological tubes are inserted into the openings at a room temperature.

6. The graft of claim 1, comprising:

a film layer formed on an inner peripheral surface of the graft and being broken when heat is applied thereto.

7. The graft of claim 6, wherein a chemical for restraining tissue fibrosis is interposed in a space between the film layer and an outer peripheral surface of the graft.

8. The graft of claim 1, wherein the photo-reactive metallic nano particles are formed in partial areas that are configured to be adhered to the biological tubes.

9. The graft of claim 1, wherein the photo-reactive metallic nano particles are formed in an entire area of the graft.

10. The graft of claim 1, further comprising:

grippers that are configured to grip opposite ends of the biological tubes along a lengthwise direction thereof.

11. The graft of claim 1, wherein the laser light has a wavelength of 650 nm to 900 nm.

* * * * *